United States Patent
Honegger et al.

(10) Patent No.: US 9,835,437 B2
(45) Date of Patent: Dec. 5, 2017

(54) LASER TUBE CUTTER WITH IN-SITU MEASURING AND SORTING

(71) Applicant: MICROLUTION INC., Chicago, IL (US)

(72) Inventors: Andrew Honegger, Chicago, IL (US); Andrew Phillip, Forest Park, IL (US); Onik Bhattacharyya, Joliet, IL (US); Kyle Stacy, Elmhurst, IL (US); Grzegorz Nowobilski, Chicago, IL (US); Kamil Szczepanik, Orland Hills, IL (US)

(73) Assignee: MICROLUTION INC., Chicago, IL (US)

( * ) Notice: Subject to any disclaimer, the term of this patent is extended or adjusted under 35 U.S.C. 154(b) by 39 days.

(21) Appl. No.: 14/801,627

(22) Filed: Jul. 16, 2015

(65) Prior Publication Data
US 2016/0016273 A1    Jan. 21, 2016

Related U.S. Application Data

(60) Provisional application No. 62/025,181, filed on Jul. 16, 2014.

(51) Int. Cl.
*G01B 11/06* (2006.01)
*G01B 11/02* (2006.01)
(Continued)

(52) U.S. Cl.
CPC .......... *G01B 11/02* (2013.01); *B23K 26/0823* (2013.01); *B23K 26/38* (2013.01);
(Continued)

(58) Field of Classification Search
CPC ...................................................... G01B 11/06
(Continued)

(56) References Cited

U.S. PATENT DOCUMENTS 2,856,997 A * 10/1958 Lafferty ................. B23D 21/14
                                                      83/190
3,657,951 A *  4/1972 Clark ..................... B23D 21/00
                                                      83/199
(Continued)

FOREIGN PATENT DOCUMENTS

| CN | 103 212 829 A | 7/2013 |
| EP | 0 914 918 A2 | 5/1999 |
| JP | 2012 040159 A | 3/2012 |

OTHER PUBLICATIONS

Written Opinion and International Search Report for PCT/US2015/040802 dated Dec. 1, 2016.
(Continued)

*Primary Examiner* — Roy M Punnoose
(74) *Attorney, Agent, or Firm* — McDonnell Boehnen Hulbert & Berghoff LLP

(57) ABSTRACT

A laser tube-cutting machine is disclosed. The tube-cutting machine may include a processing station where raw material enter the machine, a holding and positioning station configured to hold and position the raw material, at least one combined measurement and laser cutting station including a laser and at least one sensor configured to measure various aspects of the tube both before and after cutting, and an outflow processing station where cut material exit the machine.

14 Claims, 9 Drawing Sheets

(51) Int. Cl.
*B23K 26/38* (2014.01)
*B23K 26/08* (2014.01)
*B23K 101/06* (2006.01)
*A61F 2/91* (2013.01)
*G01B 11/08* (2006.01)

(52) U.S. Cl.
CPC ............. *A61F 2/91* (2013.01); *A61F 2240/00* (2013.01); *B23K 2201/06* (2013.01); *G01B 11/022* (2013.01); *G01B 11/08* (2013.01)

(58) Field of Classification Search
USPC ........................................ 356/634, 625, 635
See application file for complete search history.

(56) References Cited

U.S. PATENT DOCUMENTS

| | | | | |
|---|---|---|---|---|
| 3,776,082 A * | 12/1973 | Plegat | ............... | B23D 45/24 83/286 |
| 3,808,923 A * | 5/1974 | Plegat | ............... | B23D 25/04 83/196 |
| 4,003,278 A * | 1/1977 | Shields | ............... | B23D 21/14 226/150 |
| 4,205,569 A * | 6/1980 | Horn | ............... | B23D 21/00 83/157 |
| 4,524,656 A * | 6/1985 | Del Fabro | ............... | B21D 43/285 83/153 |
| 4,534,002 A * | 8/1985 | Urban | ............... | G06Q 10/043 700/171 |
| 4,724,733 A * | 2/1988 | Suarez | ............... | B23D 21/00 72/129 |
| 4,978,223 A * | 12/1990 | Kutchenriter | ............... | G01B 11/08 356/638 |
| 5,105,700 A * | 4/1992 | Kusakabe | ............... | B23D 25/04 83/318 |
| 5,406,870 A * | 4/1995 | Suitts | ............... | B23D 21/14 83/193 |
| 5,582,538 A * | 12/1996 | Hillestad | ............... | B23D 45/006 451/154 |
| 5,872,715 A * | 2/1999 | Bechtle | ............... | B23D 33/006 700/109 |
| 5,970,830 A * | 10/1999 | von Niederhausern | ............... | B23B 13/02 414/14 |
| 6,295,906 B1 * | 10/2001 | Kiger | ............... | B21D 43/285 83/111 |
| 6,664,499 B1 * | 12/2003 | Brink | ............... | B23K 26/032 219/121.67 |
| 9,199,336 B2 * | 12/2015 | Becker | ............... | B23K 26/38 |
| 9,491,412 B2 * | 11/2016 | Ferry | ............... | H04N 7/18 |
| 2007/0034615 A1 * | 2/2007 | Kleine | ............... | A61F 2/91 219/121.72 |
| 2007/0270996 A1 * | 11/2007 | Roise | ............... | G06Q 10/06 700/171 |
| 2011/0276171 A1 * | 11/2011 | Van Sorgen | ............... | B23Q 17/20 700/114 |

OTHER PUBLICATIONS

Machine Translation for CN103212829 A.
Machine Translation for JP2012040159.

\* cited by examiner

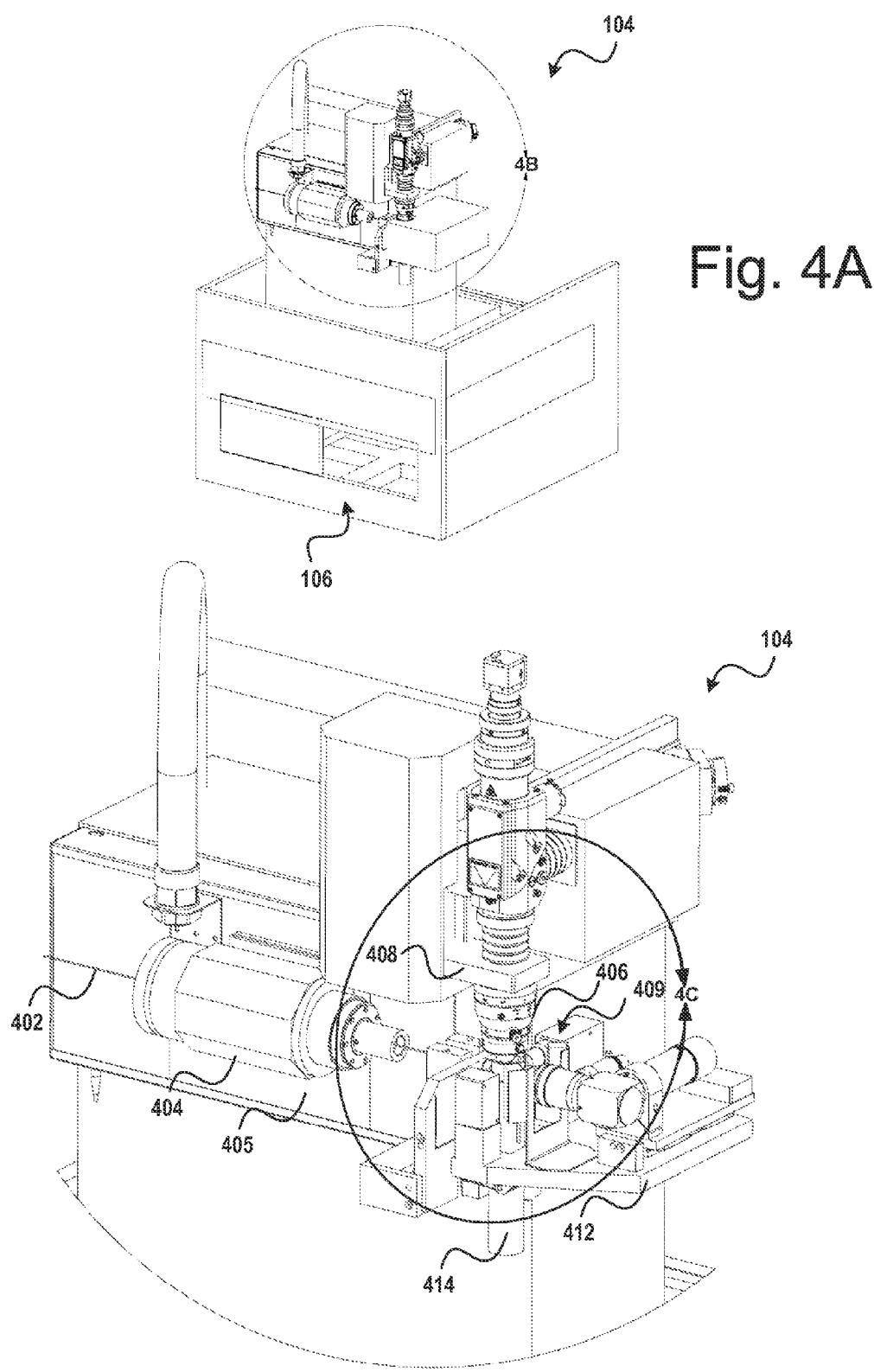

LASER TUBE CUTTER WITH IN-SITU MEASURING AND SORTING

CROSS-REFERENCE TO RELATED APPLICATION

The present application is a non-provisional application claiming priority to U.S. provisional application having Ser. No. 62/025,181 filed on Jul. 16, 2014, the entire contents of which are incorporated by reference herein.

BACKGROUND

Machine tools are used to manufacture parts by a cutting process using a variety of implements such as cutting tools, electrodes or lasers. Machine tools may be manually operated, mechanically automated, or digitally automated via computer numerical control (CNC). One type of machine tool is a tube-cutting machine for cutting long and thin tubes on a small scale.

Production of tubes for biomedical applications such as marker band and stent applications requires strict process quality, including incoming material quality, such as raw tube diameter, raw tube wall thickness, etc., and finished part dimensions, such as cut tube diameter, cut tube wall thickness, and cut tube length, for example.

Generally, the raw tube is fragile (as its shape is typically long and thin) and can be damaged during the handling process loading the tube into the cutting machine, as well as in the feeding mechanism inside the cutting machine. As a result, measuring the quality of the raw tubes before they are loaded into the machine is not sufficient to ensure overall quality. The raw tube quality is typically desired to be validated immediately prior to the cutting process to ensure no damage has occurred up-stream from the cutting process. However, if the raw tube quality cannot be measured in this way, then the finished parts must be measured down-stream from the cutting process.

In addition, the finished (cut) parts are generally small (e.g., with diameters typically between 0.010" and 0.250" and length-to-diameter ratios of roughly 1:1) and therefore these parts tend to be difficult to handle. As a result, validating the finished part quality by measuring after the cutting process has taken place is challenging.

Older generations of lasers used in tube cutting systems produced a rough cut-edge, making inspection during or directly after the cut impractical. Instead, the cut pieces first had to be cleaned (de-burred, tumbled, washed, etc.) before measurements could be taken. The latest generation of lasers used in tube cutting systems produce a clean cut-edge, making inspection during or directly after the cut practical.

SUMMARY

Disclosed herein are embodiments of a system that includes a machine for performing small-scale tube cutting applications. The machine is a single, integrated machine that performs multiple steps to cut and measure small tubes. The machine provides high-productivity, high-accuracy capability for creating and measuring small tubes.

In one embodiment, a combined laser cutting and measurement station is disclosed. This station may include a laser configured to cut a tube, a first sensor configured to take a first measurement of the tube in the cutting and measurement station either i) immediately before, ii) during, or iii) immediately after the tube is cut, a second sensor configured to take a second measurement of the tube in the cutting and measurement cutting station either i) immediately before, ii) during, or iii) immediately after the tube is cut, and a third sensor configured to take a third measurement of the tube in the cutting and measurement station either i) immediately before, ii) during, or iii) immediately after the tube is cut.

In another embodiment, a tube-cutting machine is disclosed. The machine may include a processing station where raw material enter the machine. This processing station may include a robotic system for loading the raw material into the machine. The machine may further include a holding and positioning station configured to hold and position the raw material, at least one combined measurement and laser cutting station including a laser and at least one sensor configured to take at least one measurement of the tube immediately before, during and immediately after cutting, and an outflow processing station where cut material exit the machine.

In another embodiment, a method is disclosed. The method may include determining a location of an uncut end of a raw tube just before a cutting process (M1), determining a location of a cut end of the raw tube just after the cutting process (M2), and calculating M1 minus M2 minus a kerf width to determine a cut length of a tube piece.

These as well as other aspects, advantages, and alternatives will become apparent to those of ordinary skill in the art by reading the following detailed description, with reference where appropriate to the accompanying drawings.

BRIEF DESCRIPTION OF THE DRAWINGS

Exemplary embodiments of the invention are described herein with reference to the drawings, in which:

FIG. 4A is a perspective view of various portions of a tube-cutting machine, according to an embodiment.

FIG. 4B is an enlarged perspective view of various portions of a tube-cutting machine, according to an embodiment.

DETAILED DESCRIPTION

In the following detailed description, reference is made to the accompanying figures, which form a part hereof. In the figures, similar symbols typically identify similar components, unless context dictates otherwise. The illustrative implementations described in the detailed description, figures, and claims are not meant to be limiting. Other implementations may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

The present application relates generally to machine tools, and more particularly to a machine tool configured to perform small-scale, high accuracy machining operations. In one embodiment of the present application, the machine tool is a tube-cutting machine that is configured to accurately cut tubing, whether it be into short sections or into a particular shape. Such a machine may be designed to perform tube cutting operations for a number of different applications, for example for tube sizes of about 0.010 in. diameter to about 0.250 in. diameter, tube cutting applications where dimensional measurement and validation are required for the finished parts, and tube cutting applications where very fine cut quality (edge quality, surface finish, tube cylindricity after the cut, etc.) are required. One example of applications in which the machine of the present application may be used is in biomedical applications, such as for cutting cardiac catheter marker bands and cardiac stents. However, it should be understood that the machine of the present application may also be used for additional tube sizes and for other applications than those described herein.

Figure 1:
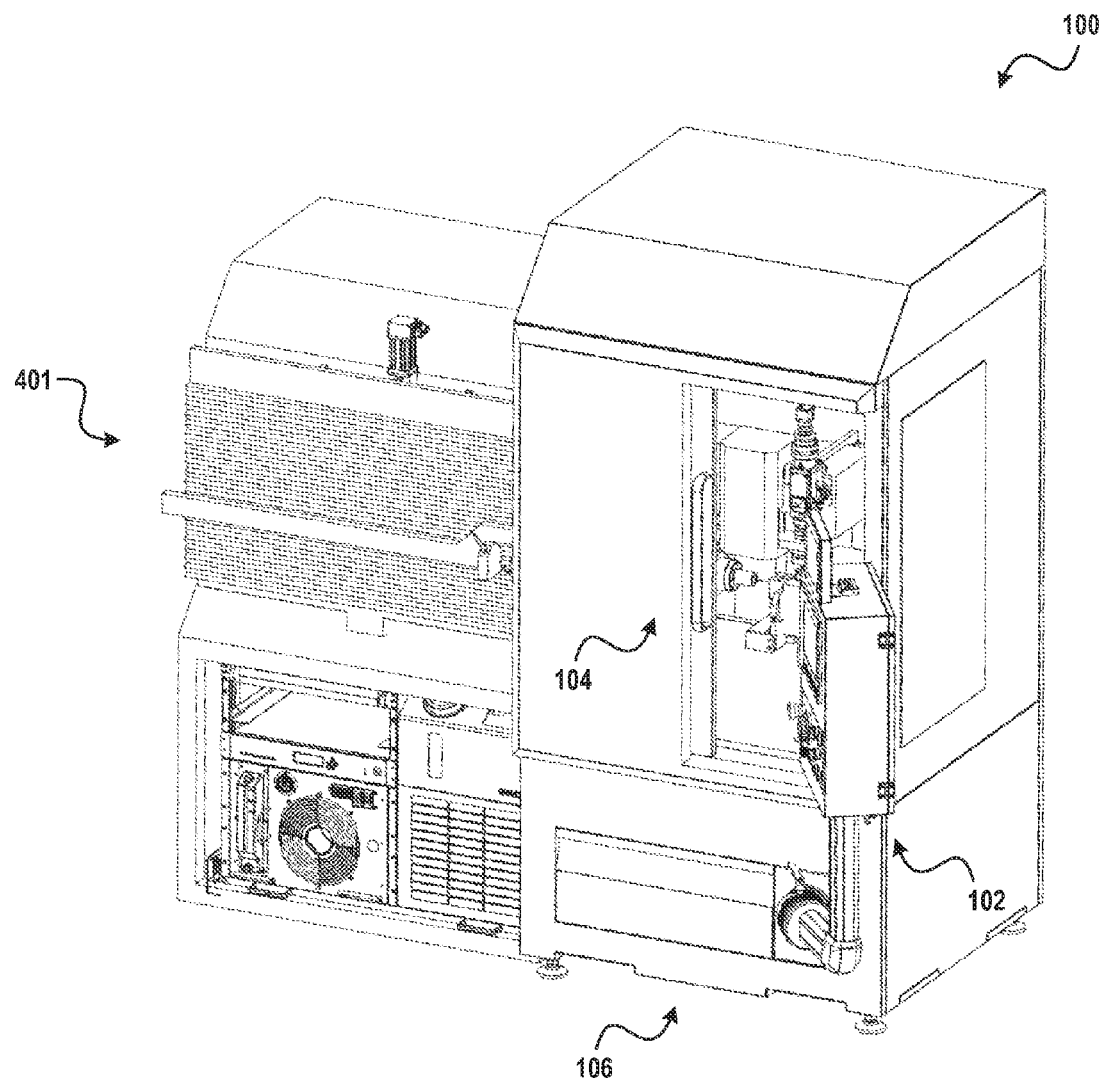
FIG. 1 is a perspective view of an example tube-cutting machine within an enclosure, according to an embodiment.
Figure 2:
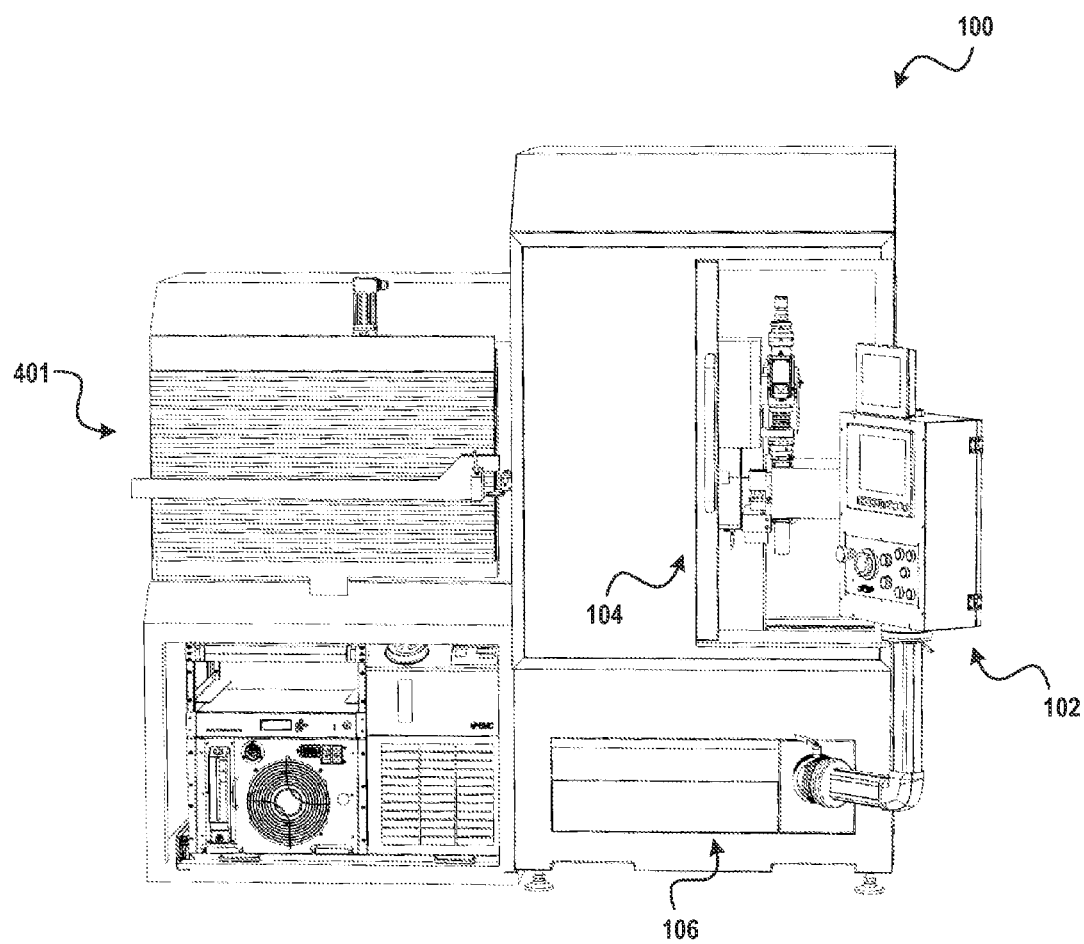
FIG. 2 is a front view of an example tube-cutting machine within an enclosure, according to an embodiment.
Figure 3:
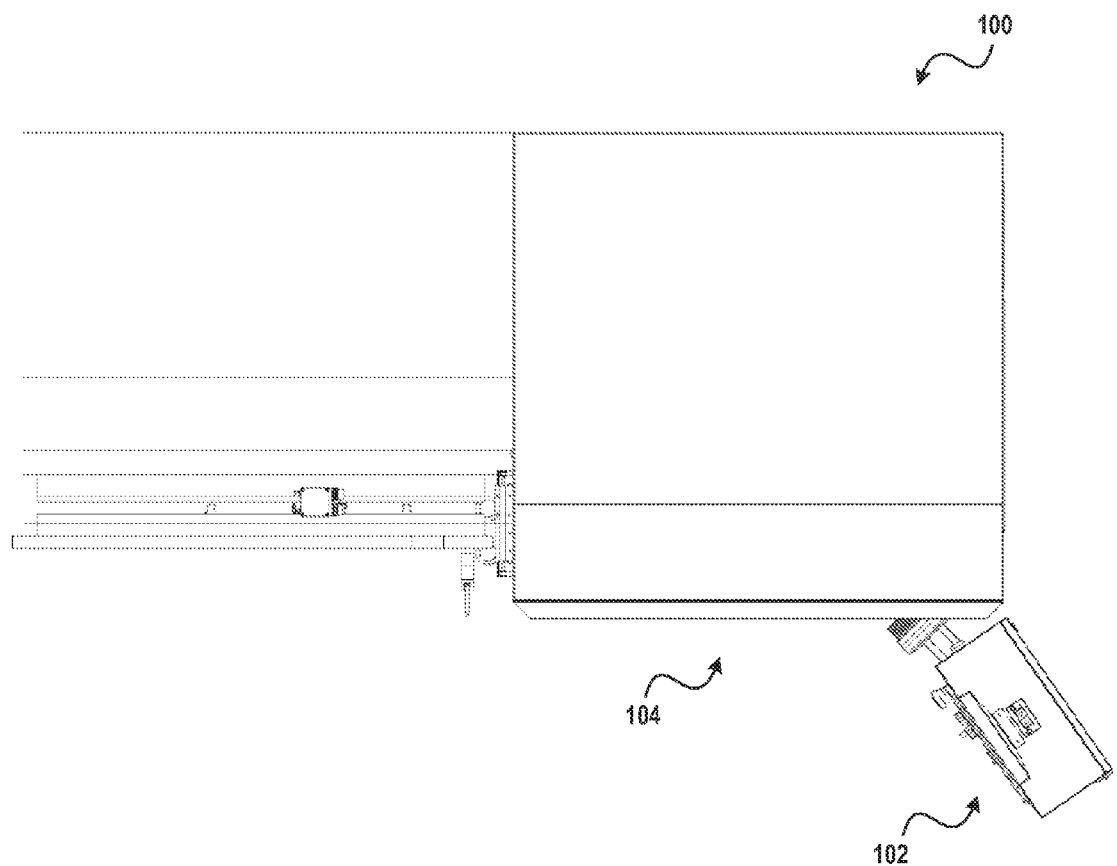
FIG. 3 is a top view of an example tube-cutting machine within an enclosure, according to an embodiment.

FIG. 1 depicts a perspective view of an example tube-cutting machine 100 within an enclosure; FIG. 2 depicts a front view of the example tube-cutting machine 100; and FIG. 3 depicts a top view of the example tube-cutting machine 100. As depicted in these figures, the machine may include a combined laser cutting and part measurement system 104, a user interface device 102 to facilitate operation and control of the laser cutting and part measurement system, and a machine component area 106 for housing various systems that operate and assist the laser cutting and part measurement system, such as power systems, part collection systems, component cooling systems, as well as others. An in-flow system or feeder may also be secured to the machine. The feeder may include one or more processing stations 401 where raw materials (e.g., un-cut, raw tubes) enter the machine.

As depicted, the user interface device 102 may be mounted on a stand, which may include various user interface components that facilitate operation and control of the laser cutting and part measurement system. Such user interface components (described further herein with respect to FIG. 6) may include one or more computing devices (such as a microcontroller or special-purpose processor), graphical user interfaces, personal computers, and/or tablet computers. These computing devices may be configured to execute programming instructions that cause various components of the laser cutting and part measurement system to operate in such as way so as to carry out a desired material processing and cutting operations. The computing devices may also be configured to collect and store measurement data collected by various sensors, and use the data to influence the behavior of the other devices in the system.

For instance, the user interface device 102 may be configured to receive an input from a user, and control the various components of the combined laser cutting and part measurement system 104 in response to this input. And the components within the combined laser cutting and part measurement system may receive control signals based on the input provided at the user interface. However, other ways to operate and control the combined laser cutting and part measurement system 104 are possible as well.

The machine may include an outer enclosure/cover. The enclosure may be made of metal, for example, although it should be understood that other suitable materials may be used. The enclosure may help prevent foreign objects from getting in the mechanisms and moving parts and to protect the machine operator from injury. In the case of laser systems, the enclosure is also used to ensure that the laser light does not escape and potentially damage anything outside the machine.

FIGS. 4A-C and 5-A-C depict perspective views of an example laser cutting and part measurement system 104 of the example tube-cutting machine 100. Further reference to the laser cutting and part measurement system 104 will be made with respect to these figures. As depicted throughout these figures, the laser cutting and part measurement system may be disposed on a granite base. As mentioned, the raw tubes may be between about 0.010 inches in diameter and about 0.250 inches in diameter, and between about 2 feet and about 6 feet long. The tubes may be made of platinum alloy, for example. In other embodiments, the tubes may be made of a Nickel-Titanium alloy. These are just example materials however, and a variety of other materials may be used.

The feeder may also include a raw material queue to hold a quantity of raw (uncut) tubes. The queue may be capable of holding a number of tubes such as 100 tubes. However, in other embodiments the queue may be able to hold a different quantity of tubes. Further, a robotic system may be used to load the raw materials from the queue into the part holding and positioning system. This robotic system may include a pair of grippers or fingers that can pick up an individual tube from the queue and feed it into the part holding and positioning system.

The tube-cutting machine may also include a part holding and positioning system. The part holding and positioning system may also be secured to the base and may include a spindle to rotate the part, and one or more linear axes to position the tube under a laser cutting head. The spindle is configured to hold and rotate a piece of tube.

Figure 4C:
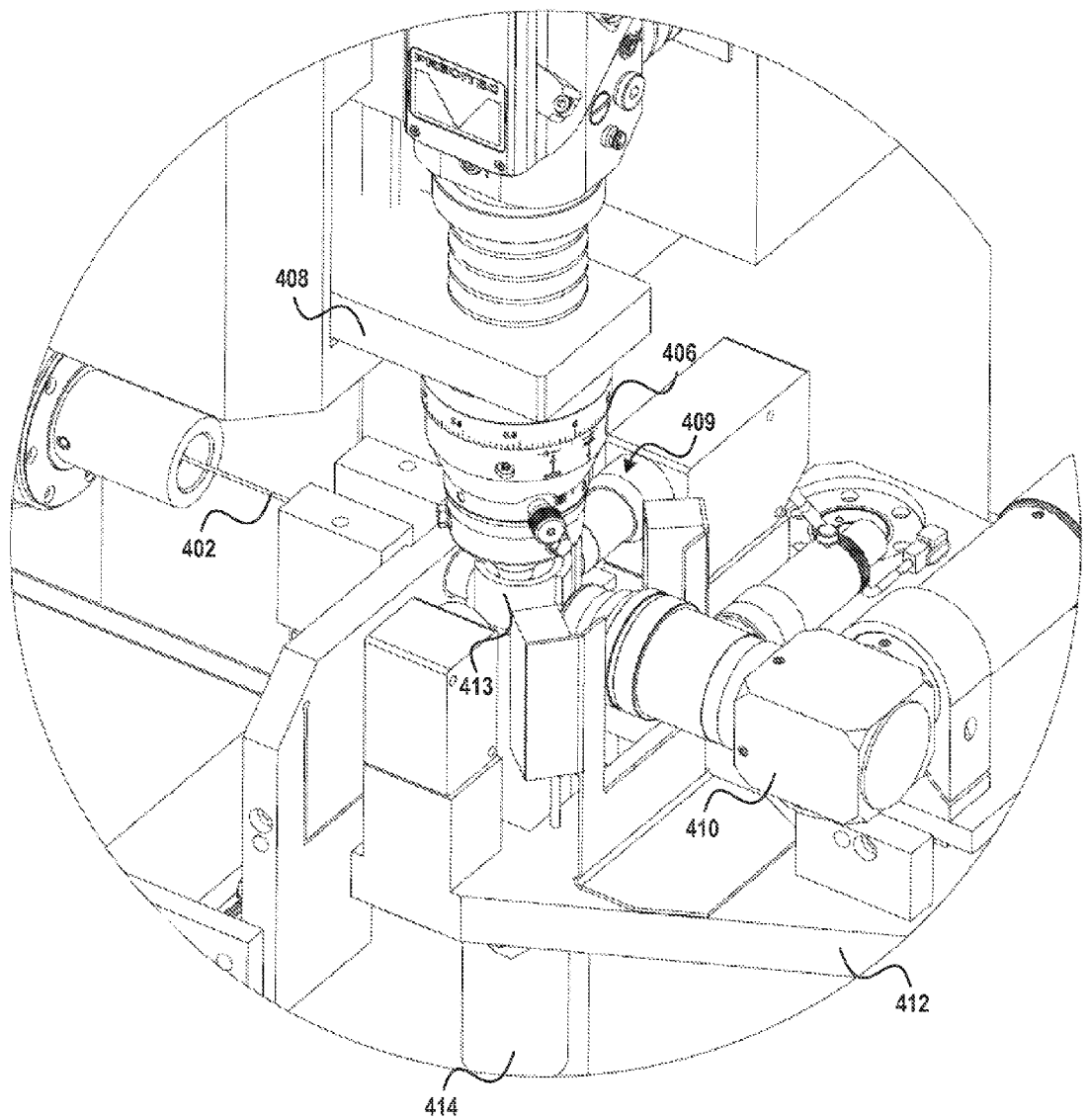
FIG. 4C is a further enlarged perspective view of various portions of a tube-cutting machine, according to an embodiment.
Figure 5A:
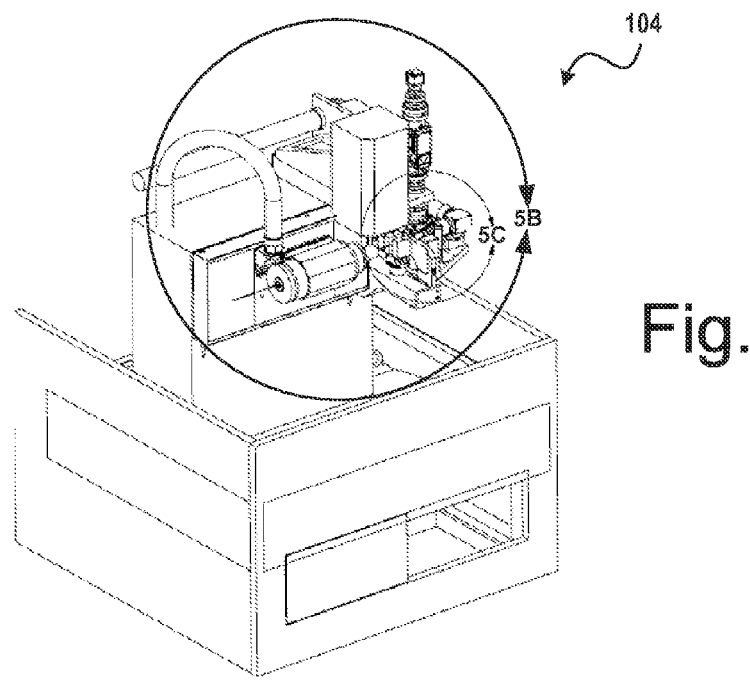
FIG. 5A is another perspective view of various portions of a tube-cutting machine, according to an embodiment.
Figure 5B:
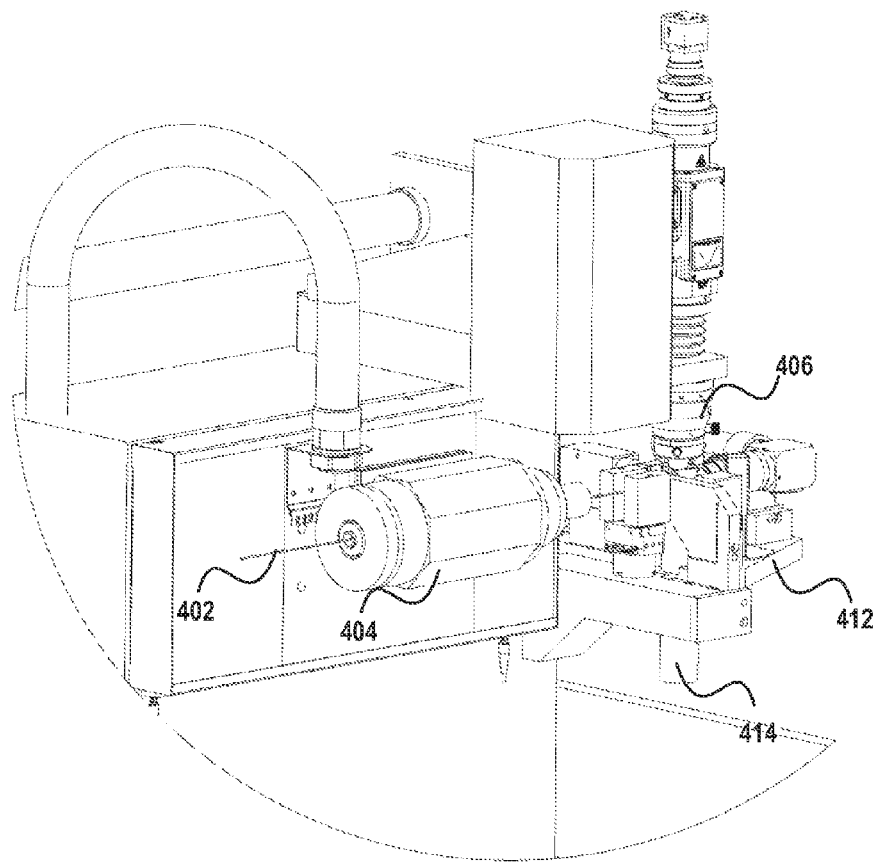
FIG. 5B is an enlarged perspective view of various portions of a tube-cutting machine, according to an embodiment.
Figure 5C:
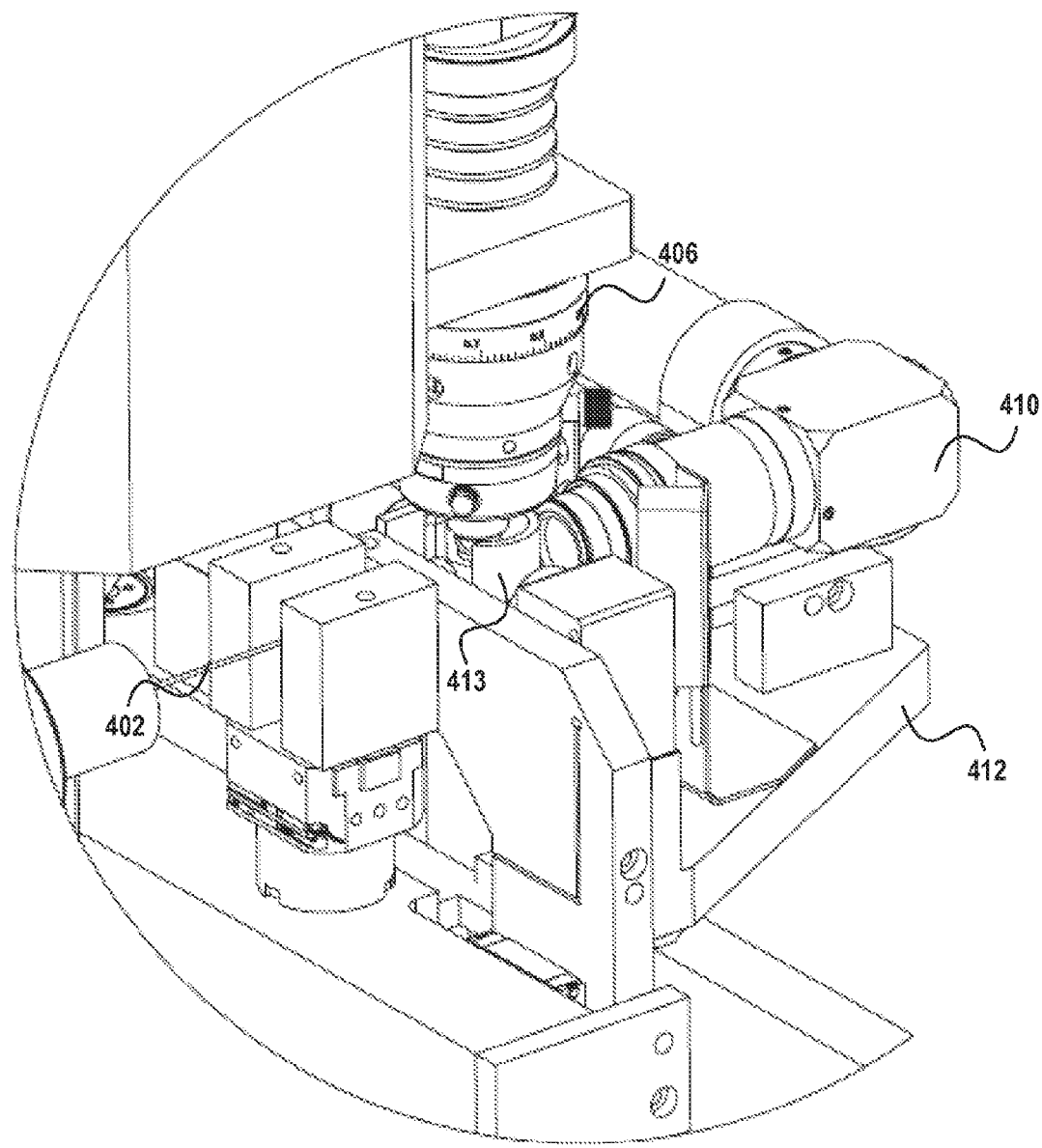
FIG. 5C is a further enlarged perspective view of various portions of a tube-cutting machine, according to an embodiment.

In operation, an operator loads raw tube stock into the feeder queue in the material in-flow system 401 of the machine. The material in-flow system robotically picks up a raw tube from the queue and feeds the tube to the part holding and positioning system. The part holding and positioning system accepts the raw tube from the in-flow system and moves the raw tube into the combined cutting and measurement zone, which is depicted more fully in FIGS. 4B-C and FIGS. 5B-C. Turning now to FIGS. 4B and 4C, these figures depict enlarged views of the combined laser cutting and part measurement system 104. The combined laser cutting and part measurement system 104 may include a spindle 404, which is depicted as holding a tube 402. System 104 may further include a laser cutting head 406, and one or more sensors 409 that may take a variety of measurements. Such measurements include, but are not limited to, the tube outside diameter, wall thickness, inside diameter, and cut length. The laser may be an ultra-short-pulse device, such as a femtosecond-pulse laser, although other lasers may be used. The laser head 406 may be coupled to a Z-stage 408, which moves vertically with respect to the other sensors. A laser cutting zone is created in the area beneath the laser head 406, as depicted in FIGS. 4B-C and 5B-C. The sensors are positioned such that they measure the tube 402 in the laser cutting zone, which enables in-situ measurement capability. A variety of sensors may be used including, for example, laser micrometer sensors, cameras, laser displacement sensors, etc. In one embodiment, three sensors are used, such as two laser micrometers and one camera. However, in another embodiment, a total of two sensors are used, one laser micrometer and one camera, with the laser micrometer sensor embodying two individual sensor measurements.

The part holding and positioning system and the cutting and measuring zone are configured so that the proper cutting and measurement processes can be achieved. As such, the tube 402 is loaded into the spindle 404 that can rotate the tube about the tube's long axis. The spindle 404 is mounted onto a linear positioning stage 405 that can move the spindle (which holds the tube) along the axis of the spindle. This linear positioning stage may be referred to as the X-stage. Other positioning stages may be present to provide other movement capabilities. The spindle 404 and X-stage 405 are able to move the tube into the measurement and cutting zone along the tube's axis, as well as rotate the tube within the measurement and cutting zone. The laser cutting head 406 may be mounted to another linear positioning stage 408 that can move the laser in a direction that is both along the laser beam and radial to the tube (perpendicular to the axis of the tube). This second linear positioning stage 408 may be referred to as the Z-stage. Thus, the Z-stage is able to move the laser focal point of the laser relative to the centerline of the spindle and tube. This allows the focal point of the laser to be adjusted and placed on the outside surface of the tube depending on the diameter of the tube.

The measurement devices within the measuring and cutting zone may be mounted in a way such that they are stationary relative to the X-, Z- and any other stages or such that they are attached to, and therefore move with the stages. For example, as shown in FIGS. 4B-C and 5B-C, a camera 410, which may be used to measure the wall thickness of the tube may be mounted to a platform 412. In this way, the camera would be positioned so that the camera can view the wall thickness of the tube depending on the diameter of the tube. Similarly, the tube length and outside diameter measurement sensors may be mounted to the machine base and not move with any of the stages. In this way, those sensors would not be affected by the motion of the X- or Z-stages.

An out-flow system may also be secured to the base, the out-flow system may include one or more processing stations where finished pieces (cut tubes) exit the system. The processing station may include a robotic part catcher and sorter, for example, to sort cut parts utilizing measurement data. The finished parts may be sorted immediately after cutting, utilizing the measurement data. For example, the measurement data may be utilized to sort parts into two categories, each with its own bin or tray. The robotic part catcher and sorter may automatically feed the cut tubes into the appropriate bin or tray depending on signals it receives from the measurement sensors.

The machine may further include a debris (waste material) management system, which removes the cutting debris and keeps the measurement sensors clean in the cutting zone. In one embodiment, the debris removal system includes a specially designed debris shield 413 that establishes an envelope around the cutting zone to prevent debris from moving outside the envelope. The shield 413 may be made of metal, plastic or some other material. The shield 413 may also include a minimum number of openings or slots that allows the laser cutting head and the measurement sensors the access they require to perform their respective tasks, but blocks off all other areas around the cutting zone.

In one embodiment, the debris management system may also include a vacuum connection 414 configured to transport the debris out of the debris management system and into some appropriate collection system. The vacuum 414 connects to the debris shield 413 and may also provide air-flow that tends to move from the outside of the shield towards the inside of the shield through the openings in the shield 413. In this embodiment, the vacuum 414 and associated air-flow will prevent the measurement sensors from becoming fouled with debris because only debris-free ambient air will be flowing past the sensors, on its way towards the openings in the debris shield and eventually to the vacuum connection and the collection system. In other embodiments, the debris shield may take on other configurations as well.

The machine may also include other devices, such as an air-knife, to protect the measurement sensors from debris. In one embodiment, the debris management system may include an air-knife to provide an air-barrier in front of the camera lens. In one embodiment, an L. E. D. ringlight may be present to provide light for the camera to take images. Other devices may also be present.

Figure 6:
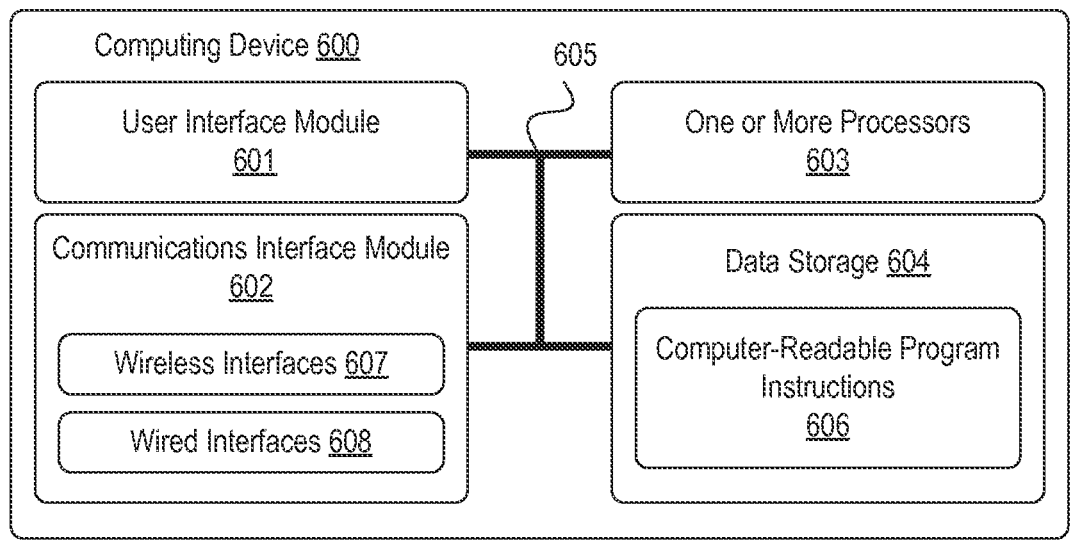
FIG. 6 is a block diagram of a computing device in accordance with an embodiment.

FIG. 6 is a block diagram of a computing device 600 in accordance with an example embodiment. For example, computing device 600 may include a user interface. The computing device 600 can include a user interface module 601, a communication interface module 602, one or more processors 603, and data storage 604, all of which can be linked together via a system bus, network, or other connection mechanism 605.

The user interface module 601 can be operable to send data to and/or receive data from external user input/output devices. For example, the user interface module 601 can be configured to send/receive data to/from user input devices such as a keyboard, a keypad, a touch screen, a computer mouse, a track ball, a joystick, and/or other similar devices, now known or later developed. The user interface module 601 can also be configured to provide output to user display devices, such as one or more cathode ray tubes (CRT), liquid crystal displays (LCD), light emitting diodes (LEDs), displays using digital light processing (DLP) technology, printers, light bulbs, and/or other similar devices, now known or later developed. The user interface module 601 can also be configured to generate audible output(s), such as a speaker, speaker jack, audio output port, audio output device, earphones, and/or other similar devices, now known or later developed. The user interface module 601 may be used to enter data for use with the methods and systems disclosed herein.

The network-communications interface module 602 can include one or more wireless interfaces 606 and/or wired interfaces 608 that are configurable to communicate via a network. The wireless interfaces 606 can include one or more wireless transceivers, such as a Bluetooth transceiver, a Wi-Fi transceiver, or other wireless transceiver. The wired interfaces 608 can include one or more wired transceivers, such as an Ethernet transceiver, a Universal Serial Bus (USB) transceiver, or similar transceiver configurable to communicate via a wire, a twisted pair of wires, a coaxial cable, an optical link, a fiber-optic link, or other physical connection to a wired network.

The one or more processors 603 can include one or more general purpose processors and/or one or more special purpose processors (e.g., digital signal processors, application specific integrated circuits, etc.). The one or more processors 603 can be configured to execute computer-readable program instructions 610 that are contained in the data storage 604 and/or other instructions as described herein.

The data storage 604 can include one or more computer-readable storage media that can be read or accessed by at least one of the processors 603. The one or more computer-readable storage media can include volatile and/or non-volatile storage components, such as optical, magnetic, organic or other memory or disc storage, which can be integrated in whole or in part with at least one of the one or more processors 603. In some embodiments, the data storage 604 can be implemented using a single physical device (e.g., one optical, magnetic, organic or other memory or disc storage unit), while in other embodiments, the data storage 604 can be implemented using two or more physical devices.

Computer-readable storage media associated with data storage 604 and/or other computer-readable media described herein can also include non-transitory computer-readable media such as computer-readable media that stores data for short periods of time like register memory, processor cache, and random access memory (RAM). Computer-readable storage media associated with data storage 604 and/or other computer-readable media described herein can also include non-transitory computer readable media that stores program code and/or data for longer periods of time, such as secondary or persistent long term storage, like read only memory (ROM), optical or magnetic disks, compact-disc read only memory (CD-ROM), for example. Computer-readable storage media associated with data storage 604 and/or other computer-readable media described herein can also be any other volatile or non-volatile storage systems. Computer-readable storage media associated with data storage 604 and/or other computer-readable media described herein can be considered computer readable storage media for example, or a tangible storage device.

The data storage 604 can include computer-readable program instructions 610 and perhaps additional data. In some embodiments, the data storage 604 can additionally include storage required to perform at least part of the herein-described techniques, methods, and/or at least part of the functionality of the herein-described devices and networks.

Turning to an example operation of the tube-cutting machine, in accordance with one embodiment, a raw tube enters the cutting and measurement zone and measurements of the tube diameter, wall thickness, tube-end position, and/or other measurements are taken by the sensors 409. The measurements may be taken immediately, or within about three (or fewer) seconds, prior to cutting. The cutting process then begins. The laser cutting works in concert with the part holding and positioning system to perform the desired cutting operation, and to generate the desired cut geometry. During the cutting process, the debris management system operates to remove the waste material from the cutting and measurement zone and to protect the measurement sensors from being fouled by debris.

Various measurements may be taken during and directly after (e.g., within 3 seconds) the cutting process to capture additional data. Measurements of the tube diameter, wall thickness, tube-end position, tube length, and other measurements are taken by the sensors 409.

In one example, the sensors include a measurement function to determine the cut length of the tube pieces. First, a sensor, such as a laser micrometer or other sensor as may be appropriate for this task, determines the location of the uncut end of the raw tube just immediately before, or within, for instance, three seconds prior to the cutting process (M1).

Next, the cutting process takes place and the cut piece of tube falls away from the cutting zone. Next, the sensor determines the location of the cut end of the raw tube just immediately after the cutting process (or within 3 seconds after the tube piece falls away) (M2). The cut length of the tube piece is equal to the first measurement (referred to as M1) minus the second measurement (referred to as M2) minus the "kerf" width. The "kerf" is a term of art and is the width of the material that is removed by the cutting process, equivalent to the "width of the saw blade." The value of the kerf width can be determined accurately and is a repeatable value, so this process can determine the cut length of the tube piece with high accuracy.

The finished piece drops into the material out-flow system. The material out-flow system utilizes data from the measurement sensors to determine if the piece is acceptable. The piece is sorted into various bins or containers.

The part holding and positioning system then resets, and the process begins again with another part of the raw tube, repeating until the entire tube has been processed. After the full tube has been processed, the sequence restarts with a new raw tube. This repeats until the queue is empty and the sequence restarts when the operator loads more raw tube stock into the queuing area.

Figure 7:
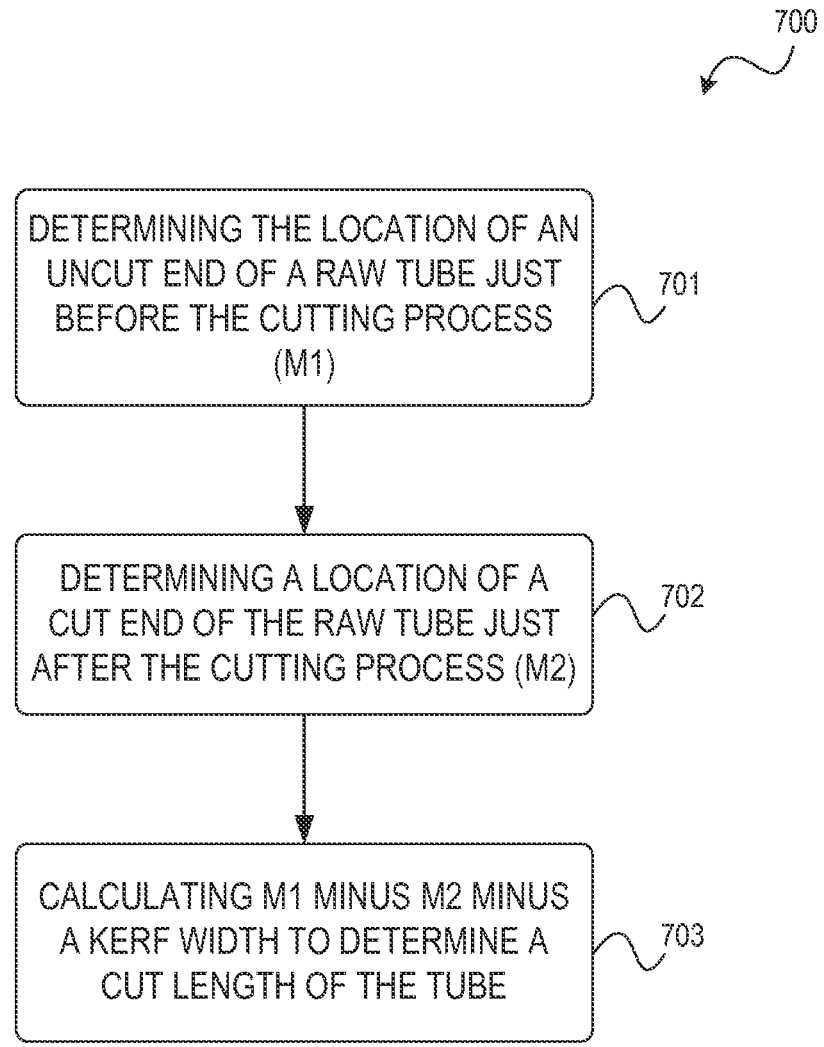
FIG. 7 depicts a flowchart of an example method, according to an embodiment.

To further illustrate the example functionality described above, FIG. 7 depicts a flowchart of an example method 700 that describes the example functionality of a tube-cutting machine in accordance with an example embodiment of the present disclosure. The example method 700 may include one or more operations, functions, or actions, as depicted by one or more of blocks 701, 702, and/or 703, each of which may be carried out by any of the systems described by way of FIGS. 1, 2, 3, 4A-C, 5A-C, and 6; however, other configurations could be used.

Furthermore, those skilled in the art will understand that the flowchart described herein illustrates functionality and operation of certain implementations of the present disclosure. In this regard, each block of the flow diagram may represent a module, a segment, or a portion of program code, which includes one or more instructions executable by a processor (e.g., the one or more processors 603 of computing device 600) for implementing specific logical functions or steps in the process. The program code may be stored on any type of computer readable medium, for example, such as a storage device including a disk or hard drive (e.g., data storage 604). In addition, each block may represent circuitry that is wired to perform the specific logical functions in the process. Alternative implementations are included within the scope of the example implementations of the present application in which functions may be executed out of order from that shown or discussed, including substantially concurrent or in reverse order, depending on the functionality involved, as would be understood by those reasonably skilled in the art.

Method 700 begins at block 701 where a sensor (such as a laser micrometer) determines the location of an uncut end of a raw tube just before the cutting process. This location may be referred to as "M1." Continuing at block 702, a sensor determines the location of a cut end of the raw tube just after the cutting process. In one implementation, this sensor is the same sensor that carried out the determination at block 701; however, in another embodiment, this sensor is a different sensor. In any case, this location may be referred to as "M2." And continuing at block 703, a computing device calculates the cut length of the tube by calculating M1 less M2 less a known kerf width. The kerf width is determined by measurement (e.g., one of the sensors measures the kerf width) or inputted into a computing device.

The present disclosure is not to be limited in terms of the particular implementations described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims.

The above detailed description describes various features and functions of the disclosed systems, devices, and methods with reference to the accompanying figures. In the figures, similar symbols typically identify similar components, unless context dictates otherwise. The example implementations described herein and in the figures are not meant to be limiting. Other implementations can be utilized, and other changes can be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

The particular arrangements shown in the figures should not be viewed as limiting. It should be understood that other implementations can include more or less of each element shown in a given figure. Further, some of the illustrated elements can be combined or omitted. Yet further, an example implementation can include elements that are not illustrated in the figures.

We claim:

1. A combined laser cutting and measurement station comprising:
    a laser configured to cut a tube;
    a first sensor configured to take a first measurement of the tube in the cutting and measurement station either i) immediately before, ii) during, or iii) immediately after the tube is cut;
    a second sensor configured to take a second measurement of the tube in the cutting and measurement cutting station either i) immediately before, ii) during, or iii) immediately after the tube is cut; and
    a third sensor configured to take a third measurement of the tube in the cutting and measurement station either i) immediately before, ii) during, or iii) immediately after the tube is cut, wherein the first measurement is a length of the tube, the second measurement is an outer diameter of the tube, and the third measurement is a wall thickness of the tube.

2. The combined laser cutting and measurement station of claim 1, wherein the first and second sensors are laser micrometer sensors and the third sensor is a camera.

3. The combined laser cutting and measurement station of claim 1, further comprising a debris management system configured to maintain the cleanliness of the sensors and remove cutting debris from the station.

4. The combined laser cutting and measurement station of claim 3, wherein the debris management system includes a vacuum connection.

5. The combined laser cutting and measurement station of claim 3, wherein the debris management system further comprises a camera lens debris control system.

6. The combined laser cutting and measurement station of claim 1, wherein the laser is an ultra-short-pulse or Femtosecond laser.

7. The combined laser cutting and measurement station of claim 1, further comprising a computing device in communication with the laser cutting and measurement station, the computing device being configured to collect and store measurement data collected by the first, second and third sensors.

8. The combined laser cutting and measurement station of claim 7, wherein the station is connected to a part catcher configured to catch and sort cut parts utilizing the measurement data.

9. The combined laser cutting and measurement station of claim 1, wherein the first sensor and the third sensor are the same sensor.

10. A tube-cutting machine comprising:
    a processing station where raw material enter the machine, the processing station including a robotic system for loading the raw material into the machine;
    a holding and positioning station configured to hold and position the raw material;
    at least one combined measurement and laser cutting station including a laser, a first sensor configured to measure a length of the raw material immediately before, during and immediately after cutting, a second sensor configured to measure an outer diameter of the raw material, and a third sensor configured to measure a thickness of the raw material; and
    an outflow processing station where cut material exits the machine.

11. The tube-cutting machine of claim 10, wherein the raw material comprises un-cut tubing and the cut material comprises cut tubing.

12. The tube-cutting machine of claim 10, further comprising a computing device in communication with the machine, the computing device being configured to collect and store measurement data collected by the at least one sensor.

13. The tube-cutting machine of claim 10, wherein the holding and positioning station including a spindle being configured to hold and rotate the tube.

14. The tube-cutting machine of claim 10, further comprising an enclosure surrounding the machine.

* * * * *